(12) United States Patent
Crowe et al.

(10) Patent No.: US 6,944,503 B2
(45) Date of Patent: Sep. 13, 2005

(54) METHOD AND APPARATUS FOR ELECTRICAL STIMULATION

(75) Inventors: Louis Michael Crowe, Galway (IE); Conor Michael Minogue, Galway (IE)

(73) Assignee: BMR Research and Development Limited, Galway (IE)

( * ) Notice: Subject to any disclaimer, the term of this patent is extended or adjusted under 35 U.S.C. 154(b) by 429 days.

(21) Appl. No.: 10/194,033

(22) Filed: Jul. 12, 2002

(65) Prior Publication Data

US 2003/0093133 A1 May 15, 2003

(30) Foreign Application Priority Data

Jul. 12, 2001 (IE) .......................................... S2001/0651

(51) Int. Cl.⁷ ................................................ A61N 1/18
(52) U.S. Cl. ........................... 607/66; 607/72; 607/46; 607/48; 607/70
(58) Field of Search .............................. 607/46, 48–49, 607/66–67, 70, 118

(56) References Cited

U.S. PATENT DOCUMENTS

| | | | | |
|---|---|---|---|---|
| 4,390,023 A | 6/1983 | Rise | ........................... | 128/421 |
| 5,109,844 A | 5/1992 | de Juan, Jr. et al. | ........ | 128/419 |
| 5,501,703 A | 3/1996 | Holsheimer et al. | .......... | 407/46 |
| 5,562,718 A | 10/1996 | Palermo | ...................... | 607/46 |
| 5,713,922 A | 2/1998 | King | .............................. | 607/2 |
| 5,895,416 A | 4/1999 | Barreras, Sr. et al. | ........ | 607/62 |
| 6,038,477 A | * 3/2000 | Kayyali | ........................ | 607/72 |
| 6,038,480 A | 3/2000 | Hrdlicka et al. | ............. | 607/116 |
| 6,393,325 B1 | * 5/2002 | Mann et al. | ................... | 607/46 |
| 6,622,048 B1 | * 9/2003 | Mann et al. | ................... | 607/46 |
| 6,748,276 B1 | * 6/2004 | Daignault et al. | ............. | 607/46 |
| 2002/0099419 A1 | * 7/2002 | Cohn et al. | ................... | 607/46 |
| 2002/0165590 A1 | * 11/2002 | Crowe et al. | ................. | 607/48 |
| 2003/0204221 A1 | * 10/2003 | Rodriguez et al. | ............ | 607/48 |

FOREIGN PATENT DOCUMENTS

| | | | | |
|---|---|---|---|---|
| WO | WO 97/47357 | 12/1997 | ............ | A61N/1/36 |
| WO | WO 00/61224 | 10/2000 | ............ | A61N/1/36 |
| WO | WO 02/22205 | 3/2001 | ............ | A61N/1/36 |
| WO | WO 01/39831 | 6/2001 | .......... | A61N/1/372 |
| WO | WO 01/43818 | 6/2001 | ............ | A61N/1/36 |

* cited by examiner

Primary Examiner—Carl Layno
(74) Attorney, Agent, or Firm—Drinker Biddle & Reath LLP

(57) ABSTRACT

Pulsed electrical stimulation is applied to selected tissues via electrodes positioned on and/or in the body. Each electrode is connected to an output (108) of the apparatus. Each output (108) is connected between a high side switch (110) and a low side switch (112) of a switching array. Each stimulation pulse is subdivided into a number of time periods. By operation of the switches (110, 112) each electrode can be selected to operate as an anode or a cathode or neither during any given time period. The spatial and/or time summation of the anode-cathode currents is controlled to selectively to stimulate selected regions and/or types of tissues, typically nerve tissues.

30 Claims, 6 Drawing Sheets

METHOD AND APPARATUS FOR ELECTRICAL STIMULATION

FIELD OF THE INVENTION

This invention relates to a method and apparatus for applying electrical stimulation to a human or animal subject.

BACKGROUND OF THE INVENTION

It is known to apply electrical stimulation with the object of producing a physiological effect, typically neuromuscular stimulation to activate or exercise a muscle, or stimulation of nerves for pain relief.

Electrical stimulation as practised hitherto is quite a blunt force. It sends electrical stimulation pulses of uniform shape, intensity and duration from one electrode to another. Some known apparatus may allow the user to vary one or more parameters such as frequency, pulse width or amplitude, but the changes are rather crude and do no allow fine control of the waveform within the body. Also, conventional stimulation techniques do not allow for precise targeting of the stimulation onto particular nerves.

It has been proposed (see for example U.S. Pat. No. 5,895,416 and U.S. Pat. No. 5,501,703) to make use of more than two electrodes in such a way as to allow the shape of the electric field to be selected from a number of options. Although these prior proposals appear to give a degree of spatial selectivity they do not permit very accurate targeting of nerves taking account of different types of nerves.

SUMMARY OF THE INVENTION

An object of the present invention is to provide an improved method and apparatus for electrical stimulation which provides a good degree of selectivity based on both spatial parameters and different types of nerves.

Accordingly, the invention in one aspect provides apparatus for applying pulsed electrical stimulation to a human or animal subject, the apparatus comprising a control circuit having a number of output terminals each of which is connectable, in use, to at least one of an array (greater than two) of electrodes placed on and/or in the subject;

the control circuit including means whereby the pulses are subdivided into a plurality of time periods, and for each time period, each output terminal may be connected as either anode, cathode or neither to provide discrimination between stimulated and non-stimulated regions of tissue and/or nerve types of the subject.

The control circuit may be operable such that the current during a single time period is unlikely to stimulate any tissue and/or any nerve type of the subject.

Preferably the control circuit is operable such that the current during a single time period is unlikely to stimulate tissue in a preselected region and/or nerve type, but the time-summated current over a number of time periods is likely to stimulate another preselected region and/or nerve type.

Alternatively, wherein the control circuit may be operable such that the current during a single time period is unlikely to stimulate a selected region of tissue and/or a selected nerve type, but the time-summated current over a number of time periods is likely to stimulate said selected region of tissue and/or said selected nerve type.

Preferably the control circuit is operable to generate a time period electrode pattern which favours the stimulation of a selected region of tissue and/or a selected nerve type Preferably also, the control circuit is operable such that the user may select a sequence of time period electrode patterns which favours the stimulation of a preselected region and/or nerve type.

Typically, a train of pulses is generated and the control circuit is operable such that some of the pulses within the train of pulses may have different time period electrode current patterns.

The circuit may be operable such that the individual time period durations and/or the number of time periods per pulse are variable.

The apparatus may include means to set the same or different total current in each time period within a pulse, and may also include means to set the current level at each output in each time period within a pulse.

The control circuit may be operable such that the current though each output is a biphasic waveform with net zero direct current component. Alternatively, the control circuit may be operable such that the current through a selected output or outputs has a predetermined DC component.

Preferably, the control circuit is operable such that the time period electrode pattern sequence creates a current density waveform in selected tissue which preferentially stimulates selected nerve types with matching temporal stimulation characteristics.

From another aspect, the present invention provides apparatus for applying electrical stimulation to a human or animal subject, the apparatus comprising a control circuit having a number of outputs each of which is connectable, in use, to a respective one of an array (greater than two) of electrodes placed on and/or in the subject;

the control circuit being arranged to generate stimulation pulses for application via the electrodes to the subject;

the pulses being subdivided into a plurality of consecutive time periods, and the control circuit including means for selectively connecting the outputs for each time period such that each of the electrodes act as anode(s) or cathode(s) or neither to provide discrimination between stimulated and non-stimulated regions of tissue and/or nerve types of the subject.

The control circuit may be operable such that during at least one time period the pulse is applied simultaneously across a plurality of outputs at one polarity and one other output at the opposite polarity such that a number of electrodes act as anodes and one electrode as a common cathode, or vice versa, whereby the intensity of the current in the region of the electrodes connected to said plurality of outputs is insufficient to stimulate that region whereas the intensity of the current in the region of the electrode connected to said one output is sufficient to stimulate the latter region.

Alternatively, the control circuit may be operable such that during different time periods the pulse is applied across respective different outputs of one polarity and a single output of opposite polarity such that electrodes connected to said different outputs act as anodes and one electrode connected to said single output acts as a cathode, or vice versa, whereby the duration of the current in the region of the electrodes connected to said different outputs is insufficient to stimulate that region whereas the duration of the current in the region of the electrode connected to said common output is sufficient to stimulate the latter region.

Preferably, the pulse is applied across different combinations of outputs in different time periods to preferentially stimulate at least two different regions of the subject in said different time periods.

Alternatively, the pulse may be applied across different combinations of outputs in different time periods to preferentially stimulate at least one region of the subject with different levels of stimulation during said different time periods.

The total current flowing, in use, across the electrodes may be substantially constant over all time periods of a pulse, or may differ for at least one time period of a pulse.

The invention, in a further aspect, provides an apparatus as defined above in combination with a plurality of electrodes. Preferably, at least one electrode has a different area to the others. In one embodiment at least two of the electrodes are intertwined.

The apparatus preferably includes memory means for storing timeslot pattern sequence data.

Another aspect of the present invention provides a method of applying electrical stimulation to a human or animal subject, comprising placing a plurality of spaced stimulation electrodes on and/or in the subject, each electrode being capable of selectively acting as an anode, a cathode or neither, and applying electrical stimulation pulses to the subject via the electrodes, the duration of each pulse comprising a plurality of consecutive time periods during each of which none, some or all of the electrodes are selected to act as anode(s) or cathode(s) or neither to provide discrimination between stimulated and non-stimulated regions of tissue and/or nerve types of the subject.

In one form of the method, during at least one time period the pulse is applied simultaneously across a plurality of electrodes at one polarity and at least one other common electrode of the opposite polarity whereby the intensity of the current in the region of said plurality of electrodes is insufficient or unlikely to stimulate that region whereas the intensity of the current in the region of the common electrode is sufficient to stimulate the latter region.

In another form of the method, during different time periods the pulse is applied across respective different electrodes of one polarity and a common electrode of opposite polarity, whereby the duration of the current in the region of said different electrodes is insufficient or unlikely to stimulate that region whereas the duration of the current in the region of the common electrode is sufficient to stimulate the latter region.

The pulse may be applied across different combinations of electrodes in different time periods to preferentially stimulate at least two different regions and/or nerve types of the subject in said different time periods.

Alternatively, the pulse may be applied across different combinations of electrodes in different time periods to preferentially stimulate at least one region and/or nerve type of the subject with different levels of stimulation during said different time periods.

The invention improves upon the prior art by making use of the phenomenon of the time dependency of nerve excitation. Excitable tissues, such as nerve membranes, maintain an electrical potential across their membranes by means of ionic pumps which establish a concentration difference of certain ions between the inside and outside of the cell. With the membrane at rest, typically this is of the order of −70 mV, with the inside of the cell being more negative than the outside.

If the potential is reduced to about −50 mV the nerve membrane will spontaneously discharge as a result of a sudden increase in ion permeability. This action induces depolarisation further along the nerve, and in this way the signal is propagated along the nerve. It is therefore a triggering action, with the trigger condition being the reduction in the membrane potential from its resting level of −70 mV to the trigger level of −50 mV.

Achieving the local trigger conditions therefore involves the transfer of an amount of charge, and this in turn means that a certain current must be maintained for a certain amount of time. Different types of nerves have different trigger characteristics. Not only do they respond differently to the total Coulombs per pulse, but also respond differently to how these Coulombs are passed, i.e. the duration and the shape of the waveform that the individual nerve perceives.

This is a four-dimensional problem with three spatial dimensions and a time dimension, which may be represented by the vectors $E(x,y,z,t)$ Electric field vector, and $J(x,y,z,t)$ Current density vector.

This means that the control of the electric field intensity alone is insufficient to control the triggering of nerve membranes. Viewed local to any target membrane, the trigger conditions are that the magnitude and direction of the local current density are such as to depolarise the target membrane, and further that the time integral of the current density vector at the target location is sufficient to reduce the transmembrane potential to the trigger level.

It is known that different nerves have different characteristics that make them relatively more or less susceptible to stimulation from a particular waveform. Thus by managing the local current density vector we can selectively excite one type of nerve in preference to another. For example, a very low level current density vector will not trigger a nerve that 'accommodates' very quickly but will activate other nerves.

Therefore, control of excitation in a three-dimensional body part using an array of electrodes requires management of the time dimension of the current density vector in addition to the spatial dimensions. This offers possibilities for differentiation between nerve fibres with different trigger characteristics.

BRIEF DESCRIPTION OF THE DRAWINGS

Embodiments of the invention will now be described, by way of example only, with reference to the drawings, in which.

DETAILED DISCUSSION OF THE PREFERRED EMBODIMENTS

Figure 1:
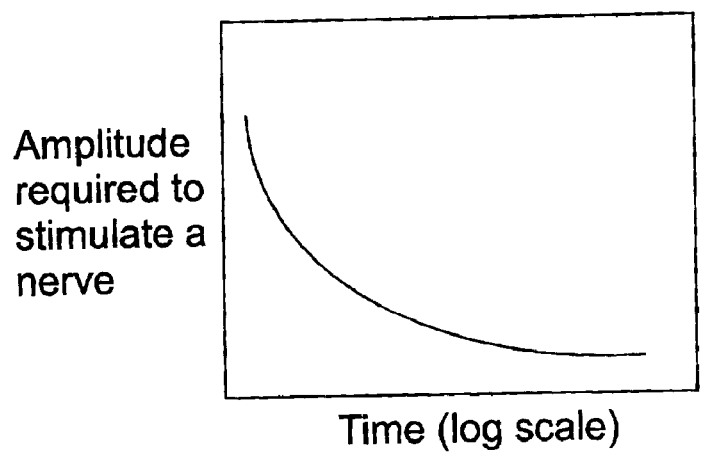
FIG. 1 is a graph of intensity against duration, used in explaining the background to the invention.

Although it is an oversimplification, nerves can be regarded as acting like digital devices, i.e. they are either stimulated or not. FIG. 1 is an intensity-duration graph of the signal amplitude required to produce stimulation. For short duration pulses, a large intensity (pulse amplitude) is required to stimulate a nerve. The intensity required rapidly diminishes as the pulse duration is increased. For longer pulses the required intensity plateaus out, i.e. prolonging the pulse beyond a certain point has little effect on the likelihood of stimulating a particular nerve.

Each nerve has its own graph, but generally it is of broadly similar shape but displaced. Two adjacent nerves may be exposed to a similar pulse sufficient to stimulate one nerve not the other, because one has a lower stimulation threshold. A third nerve, nearby, may have yet a lower stimulation threshold yet not be stimulated because its position is such that the pulse reaching it is attenuated to below the stimulation threshold for that nerve.

The present embodiments of the invention use discrete pulses of electrical energy which are applied repetitively to a subject. The pulses are repeated at a repetition frequency of typically 5 to 50 Hz, depending on the therapy. Each pulse is divided into a number of time periods or time slots, there being four time slots per pulse in the following examples.

An array (greater than two) of electrodes are selectively activated during the occurrence of the pulse to produce a pattern of electrical activity between them. Different combinations of electrode pairs may be used during successive time slots to produce a greater number of potential stimulation therapies the number of electrodes.

In each time slot the stimulation current goes 'from' one or more electrodes 'to' one or more other electrodes. Each electrode the current is coming from in any given time slot is at that time acting as an anode and is designated HIGH (h). Each electrode the current is going to in any given time slot is at that time acting as a cathode and is designated LOW (l) or SINK. An electrode that is not active in any given time slot is designated OFF (X). Each electrode can be selectively switched on-high (H), on-low/sink (L) or off (X) in any combination in each time slot.

In the examples given below constant current stimulation pulses are used. In other words, the total current flowing from all on-high (H) electrodes is substantially constant for all time slots. For example, if the total pulse current is 1, in a time slot where two electrodes are H there will be a current of I/2 flowing from each, in a time slot where three electrodes are H there will be a current of I/3 flowing from each, and so on. As the timeslots used can be as short as 1 microsecond, the currents and voltages chosen for the array of electrodes can be much higher than would typically be used with electrical stimulation may safely be used. The voltage range used in the present embodiments is between 1 and 120V DC and the current range presently being used is between 1 and 0.2 amps. Those knowledgeable in electrical stimulation will understand that a similar technique is applicable using a constant voltage stimulator. The effects of the invention will then be somewhat different but predictable. For instance, the current through a particular pad may not drop when another is added in.

It should also be noted that while most of the examples given are related to neuromuscular stimulation this invention is equally applicable to any form of electrical stimulation.

In the embodiments of the invention there are two types of summation: spatial summation and temporal summation. Spatial summation is said to happen when two or more electrodes are on during the same time period. Temporal summation is said to happen when a signal accumulates over more than one time slot at a given location. It will be clear that although the word summation is used that sometimes the effect is to reduce, not increase, the current at a particular locus.

Figure 2:
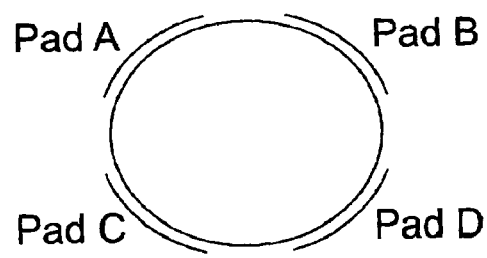
FIG. 2 is a schematic diagram of electrodes placed on a nerve bundle.

Table 1 shows some basic examples of the method according to the invention where electrodes A, B, C and D are affixed to a nerve bundle as shown in FIG. 2. It will be understood that in each example in Table 1 (and in the examples shown in Table 2 and 3 to be described) the configurations of the electrodes (H, L or X) in the four consecutive time slots correspond to the duration of a single pulse only in each case. In practice, the pulses (and timeslots) will be repeated for anything up to an hour or more at a repetition frequency of, typically, anything from 5 to 50 Hz, depending on the therapy. Also, although each pulse is shown as extending over four time slots in the examples, there may be more or fewer time slots per pulse according to the desired therapy.

In Example 102 electrodes A and B are both on together for time slot 1. Current passes from these and sinks in electrode C. During this time slot electrode D is not active. For a given total current the effect of this is to reduce the current density seen under pads A and B but not C.

If D is activated in time slot 1, Example 103, the effect of this is to further reduce the current density directly under A and B. In a constant current stimulator the total current would remain the same, therefore the amount of current sinking at C would be the same. However, the relative sizes, positions and the properties of the electrodes and the characteristics of the substance between them determine the field between them, current pathways and intensities at any given point.

Example 104 is an example of temporal summation. In time slot 1 A is high, C is low, and B and D are off. In time slot 2 A is off (x), but B is high, C is still low. D is off. In this example the current seen under pad C may be of sufficient intensity and duration to stimulate a nerve in the region adjacent C. However, in the regions adjacent A and B it is of insufficient duration to stimulate nerves.

The two forms of summation may be combined as in Example 106. In time slot 1 A and B are high and C is low; in time slot 2 A and B are off and D is high.

It will be evident that the shape of the signal (at a given locus) may be varied by selectively switching the electrodes high, low or off over designated time periods. The shape of the pulse is known to affect stimulation.

Some wave shapes are thought to allow greater activation of particular types of nerves.

For example, in Example 107, the current perceived under C is approximately an ascending staircase shape with a sudden cut off. In Example 108, the shape of the current under C is hat-shaped. By increasing the number of time slots and electrodes an almost infinite number of pulse shapes are possible.

The number of electrodes may be varied, giving a much wider range of possibilities. The invention is applicable to almost any arrangement of electrodes. The individual requirements may determine the optimal orientation of the electrodes.

Figure 3:
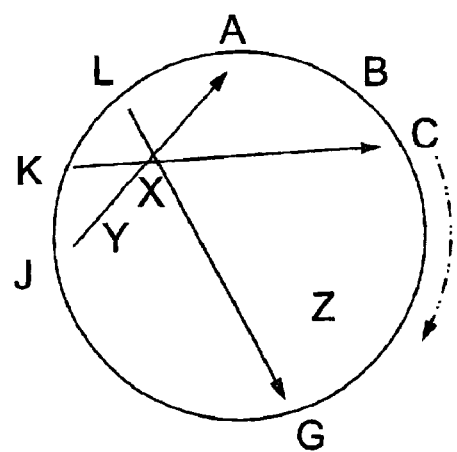
FIG. 3 is a schematic representation of an electrode array.

For example, FIG. 3 is a schematic representation of an electrode array in which the circle represents a nerve bundle with twelve electrodes (A to L, not all shown) are arranged around the nerve. Inside this bundle there are many nerves fibres. It is intended to stimulate nerve fibre X but not nerve fibre Y.

In this example, see Example 110, Table 1, J, K and L are respectively high for time slots 1, 2, 3. Their sinks are A, C and G respectively. In this example the time slots are all 30 microseconds. At the current intensity chosen 30 microseconds is not long enough to stimulate a nerve. However, the nerve at position X 'sees' current for 90 microseconds (it is not necessary for the pulses to be exactly aligned, however their alignment or lack thereof has an effect on the stimulation). 90 microseconds is long enough to stimulate X but not its neighbours.

It will be appreciated that the same technique could equally apply using external electrodes. For instance, the array of electrodes may be placed around the leg, and area X may represent the sciatic nerve. The sciatic nerve is then stimulated but the other nerves of the leg are not. In a similar way individual nerve or nerves going to or in body areas/organs may be targeted.

Figure 4:
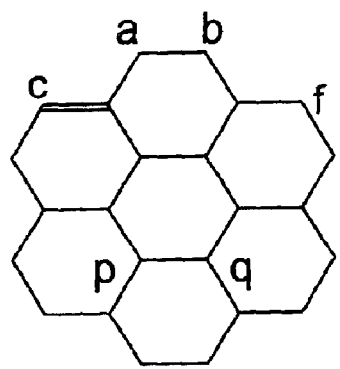
FIG. 4 shows an array of electrodes in a hexagonal arrangement.

The electrodes may be arranged in any format, in 2 or 3 dimensions, for instance a grid or a wall of hexagons or a latticework, see FIG. 4.

The electrodes may be within the structure to be stimulated, external to it or a combination of both.

Figure 5:
FIG. 5 shows a set of electrodes which differ in size.

It should be noted that the electrodes are not necessarily the same size. For example, in FIG. 5 the electrode A is twice the size of B or C. Thus, for a given amount of current going to C in one time slot the current will be more spread out under the A than it is under B in another time slot. In addition, the electrodes may be orientated in relation to each other in order to further augment or diminish the current felt under them.

Figure 6:
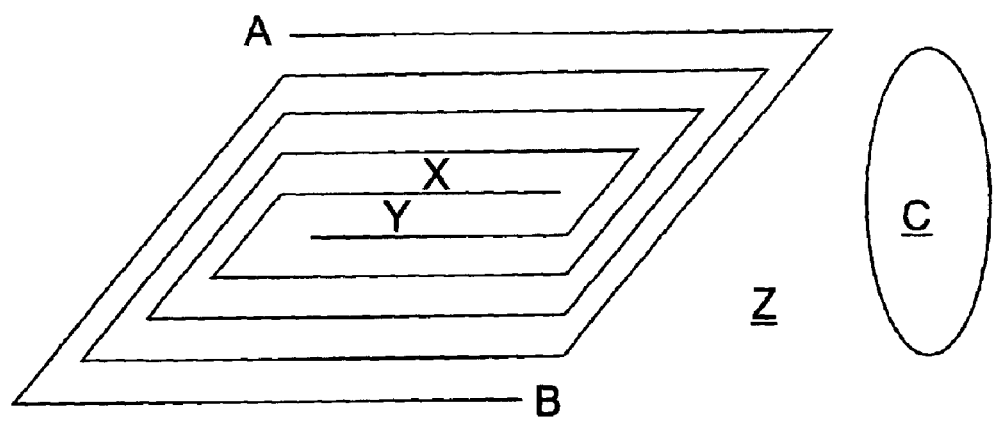
FIG. 6 shows intertwining electrodes.

The electrodes may intertwine in some way. For instance, in FIG. 6 electrodes A, B and C are on the skin. It is desirable to send current from the area covered by electrodes A and B to electrode C, without stimulating the superficial pain fibres under A and B (points x and y). But it is wished to stimulate deeper nerves, say located at z. In this example the current is on for 50 microseconds under A and B in consecutive time slots, at an intensity chosen too low to stimulate a nerve there. However, deeper down, at point z, as the current goes towards C the currents "merge" and stimulate the nerves at these depths as they 'see' a current for 100 microseconds. More and more electrodes may be added, giving greater control and selectively. They may intertwine as shown or be adjacent to each other or apart.

The electrodes A, B and C may be discrete electrodes, cut to interlock with each other, or they may share a backing, and/or the same contact material with the skin. The important part is that they act as different units electrically, so that most of the current is not spread over the whole area of the combined electrodes. For instance, they could be wires or conductive material printed onto the back of silicone rubber or PVC. The electrical properties of the material may be altered by the amount of carbon in the rubber/PVC. When used as an electrode there should be a rapid fall off in the current as one moves away from the electrode that is designated as H in the relevant time slot.

Pulses have one or two phases, an out and a return to balance things electrically. These may be symmetrical (equal but opposite) or asymmetrical. If there is a gap between the phases this is known as an interphase delay. In the examples given biphasic symmetrical pulses were used. This was achieved by following timeslot 4 with an equal but opposite pulse.

However, to those knowledgeable in the field it will be evident that the pulses could be monophasic or biphasic asymmetric. It will also be clear that depending on how the array of electrodes were designated high/low/off in the timeslots that some loci could see one type of pulse, e.g. monophasic, whilst other loci could see another, e.g. symmetrical biphasic. It may also be seen how some loci could see no net DC current whilst other areas could have a net DC. This may be useful in reducing skin rashes associated with net DC while allowing deeper tissues to benefit of net DC therapies. Indeed, the invention allows one to vary most stimulation parameters at any given locus. By way of example, it may be deemed desirable to have a shorter inter-phase delay in the area close to one pad. In this scenario this pad is designated off (X) for the last time slot while other pads remain active (or the first time slot if one is simply repeating with reversed polarity the second phase of the pulse). Extended and/or multiple time slots symmetric, asymmetric, monophasic, biphasic, multiphasic, etc. pulses may be used. So for instance certain loci may see a higher frequency of pulses than others.

Referring back to the intensity-duration figure, it will be clear that beyond a certain pulse width at a given intensity there is relatively little additional effect to prolonging the pulse for a given type of nerve. A pulse going from a pad A may go to a pad B for, say, 500 microseconds. Pad A may then remain active for a further 100 microseconds going to a pad C, with pad B switched off. The extra 100 microseconds has little additional effect in the vicinity of pad A; however, the area near pad C sees 100 microseconds which is enough to stimulate nerves in this area. Thus pad A stimulates separately two different areas without doubling the number of pulses or the rate at which the nerves in its area of influence are fired. An alternative method to achieve the same effect is the sending of a second pulse from pad A but within the absolute or relative refractory periods of the nerves in its sphere of influence. After being stimulated, nerves take a little while to recover before they can be stimulated again (absolute refractory period), and for a short time thereafter the amount of current required to stimulate a nerve is greater than normal (relative refractory period). These will be known to those involved in research in electrical stimulation.

By adding in random elements, within certain limitations, to the switching mechanisms it will be clear that the issue of accommodation may be addressed.

Suitable treatment units for administering the treatments described herein will vary depending on the treatment environment. For example, where the unit is employed to provide muscle stimulation, then a conventional type device such as a NT2000 treatment unit from Bio-Medical Research Limited, Ireland can be used. Software can be included in such unit to allow the unit to be programmed to generate the required pulses and execute the required switching between electrodes in different time slots.

Such a unit has two main forms of user-control, or a combination of these. The unit may be partly or fully programmable. The user may be able to input many of the variables as seen in the Tables. The intensity of the pulse current during each time slot may be varied or the length of the individual time slots may be varied. Also, the intensity through a particular pad or pad(s) may also be varied. Also, through spatial or temporal summation as discussed, including effects on the interphase delay, the shape of the current waveform perceived at a given locus may be varied, e.g. staircase or hat-shaped as described earlier.

Alternatively, the workings of the unit may be hidden from the user. This is particularly suitable with the use of dedicated electrodes especially when pre-positioned or reliably repositionable, as in conjunction with a garment. The user interface may indicate simply a change in a particular pad/area or muscle group. Software then transforms this into changes in the Table executing the desired effect.

Figure 7:
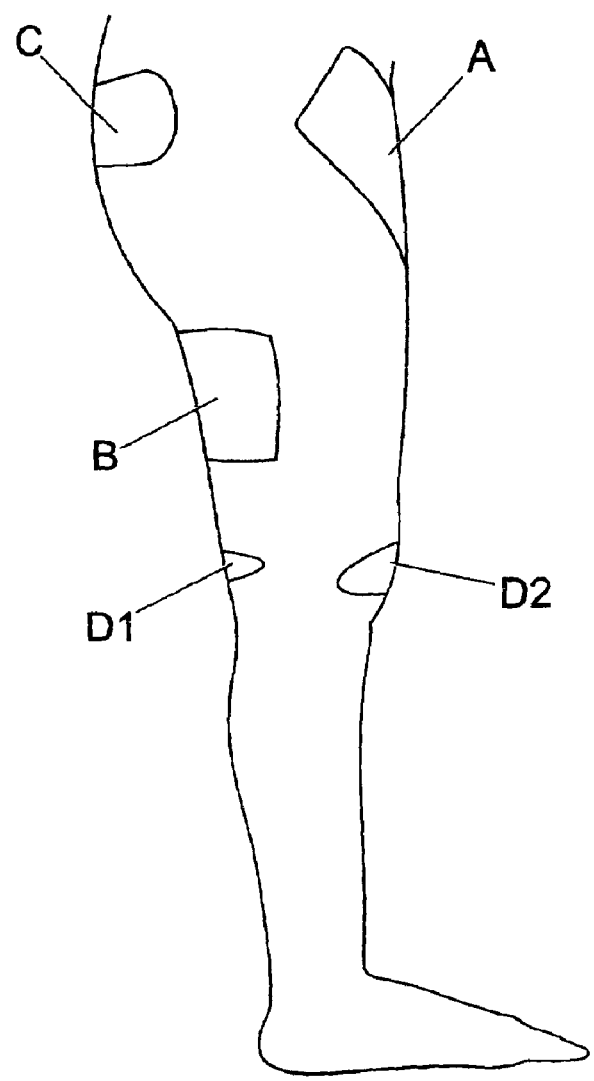
FIG. 7 illustrates a first arrangement of electrodes attached externally to a subject's leg.

FIG. 7 illustrates pads A to D attached externally to a subject's leg, and Table 2 one possible stimulation regime for that arrangement of electrodes comprising a warm up phase and nine successive treatment phases. The durations shown in the table are in microseconds and the repetition rate of the pulse is 8 Hz. Pad A sits on the upper quadriceps and stimulates this muscle (the main muscle bulk at the front of the leg), in particular the upper fibres. It lies at an angle of 30 degrees and is 10×20 cm in area. Pad B, 10×20 cm in area, is across the hamstrings (back of leg), horizontal. Pad C, 15×7 cm in area, sits on the maximum convexity of the glutei. Pad D has 2 discrete components D1 and D2; these are electrically joined. The anterior portion D2, 15×3 cm in area, sits on the front of the leg above the knee, horizontal. The posterior portion D1, 7×5 cm in area, sits above the back of the knee.

As the treatment shifts from one phase to the next the subject literally feels the balance of contraction moving from one area of his lower limbs to the next. Indeed at high intensities the whole body can rock or shift position as you move from one arrangement to the next. For example, at approximately 50% of maximum unit intensity specified above, in phase 6 the heel of the foot may be firmly planted on the ground; shifting to phase 7 immediately lifts the subject up onto tip-toes as it brings in more calf contraction.

Referring now to Table 2, phases 1, 2 and 3 are very similar, phases 2 and 3 being included mainly to take some pressure off the hamstrings (pad B) as these can get tight in some subjects. Phases 4 and 5 have a much stronger gluteal component, while phase 6 has a heavy emphasis on quadriceps contraction at the expense of the other muscles. Phase 7 and 8 bring back a more balanced contraction, while phase 9 gives a very strong upper quad and hamstring contraction, and a moderately good gluteal contraction. Despite not having D active the calf muscle is still contracting well as the time slot 3 arrangement (A:H, B:L, C:H) is particularly good at catching the sciatic nerve (supplying the calf) in the upper leg when followed by B:L, C:H in time slot 4.

Figure 8:
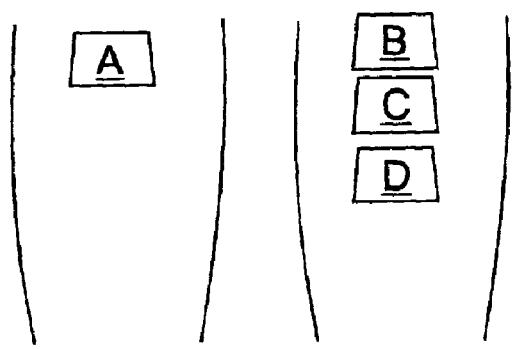
FIG. 8 illustrates a second arrangement of electrodes attached externally to a subject's leg.

FIG. 8 shows a further arrangement of electrodes A to D attached to a subject's leg, and Table 3 a corresponding stimulation regime. The electrodes are standard, off-the-shelf, adhesive pads, 10×7 cm in area. A is positioned on the right leg; B, C and D on the left as in the figure. The duration shown in the table are in microseconds.

Example 1 is equivalent to the traditional set-up where current goes from A to B causing broadly similar contractions at A and B. The duration of the pulse is 90 microseconds.

Example 2 provides contraction in the right leg but apparently nothing in the left. This is because the current density at A is as Example 1 for the full 90 seconds. However, even though pads B, D, D each have the same area as A and experience the same current intensity no nerve fibres in their vicinity are stimulated as each only experiences it for 30 microseconds, not long enough to reach the threshold for this intensity. Example 3 is similar.

In Example 4 the contraction of the right leg is lessened (versus Examples 2 and 3). At the chosen intensity this has no effect on B, but the simple change in polarity at A for the first 30 microseconds diminishes the contraction at A.

Examples 5 and 6 show that variations during a pulse, using a middle time-slot to shape the wave, have a very large effect.

Example 5 shows that by simply changing the polarity at time-slot 2 can bring about large effects. Example 6 shows that flipping the polarity at A (time slot 3) is not the same as disconnecting it.

In the foregoing, where we say that a contraction is obtained in one area but not another that is in relation to a particular chosen current intensity. Obviously, at a high enough intensity, using time slots of 30–50 microseconds, a contraction could be obtained at any electrode.

Figure 9:
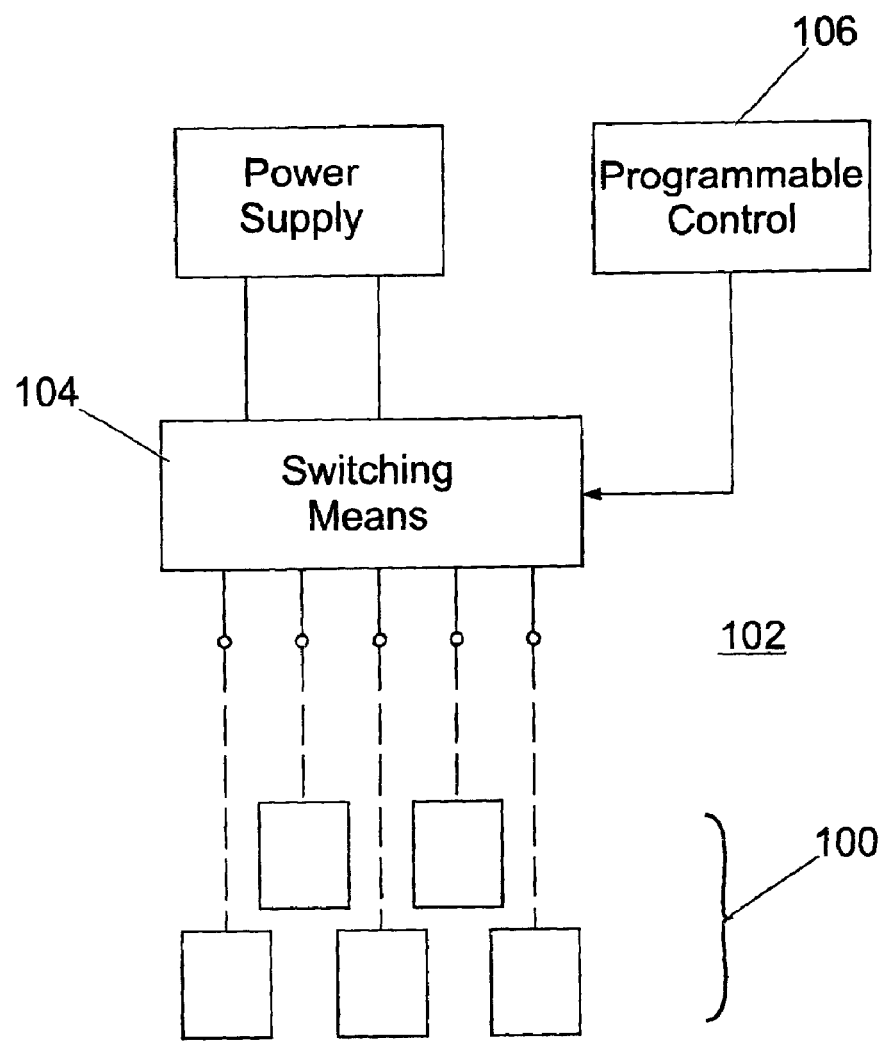
FIG. 9 illustrates the principle of one form of apparatus for carrying out the invention.
Figure 10:
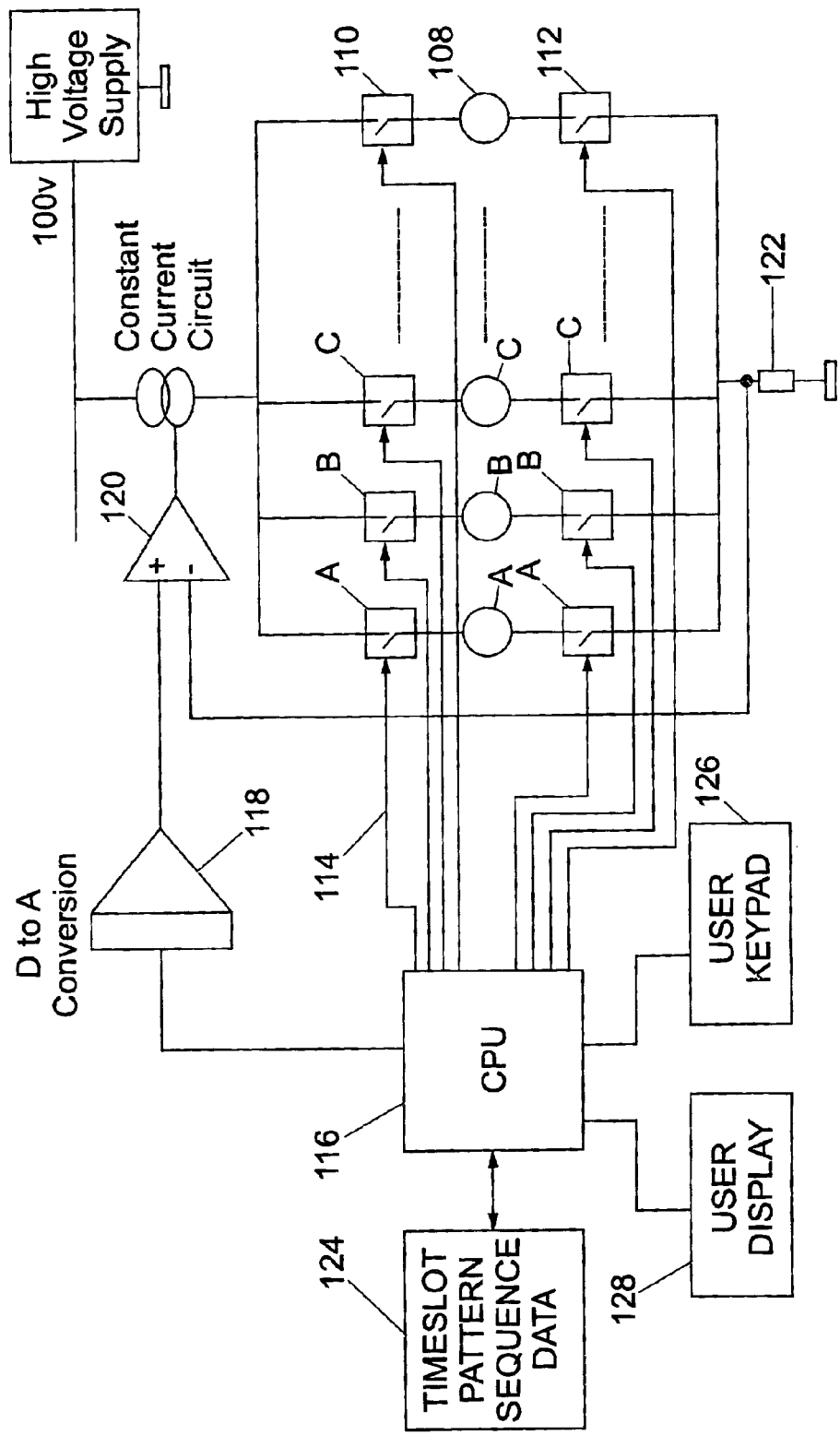
FIG. 10 shows one embodiment of apparatus.
Figure 11:
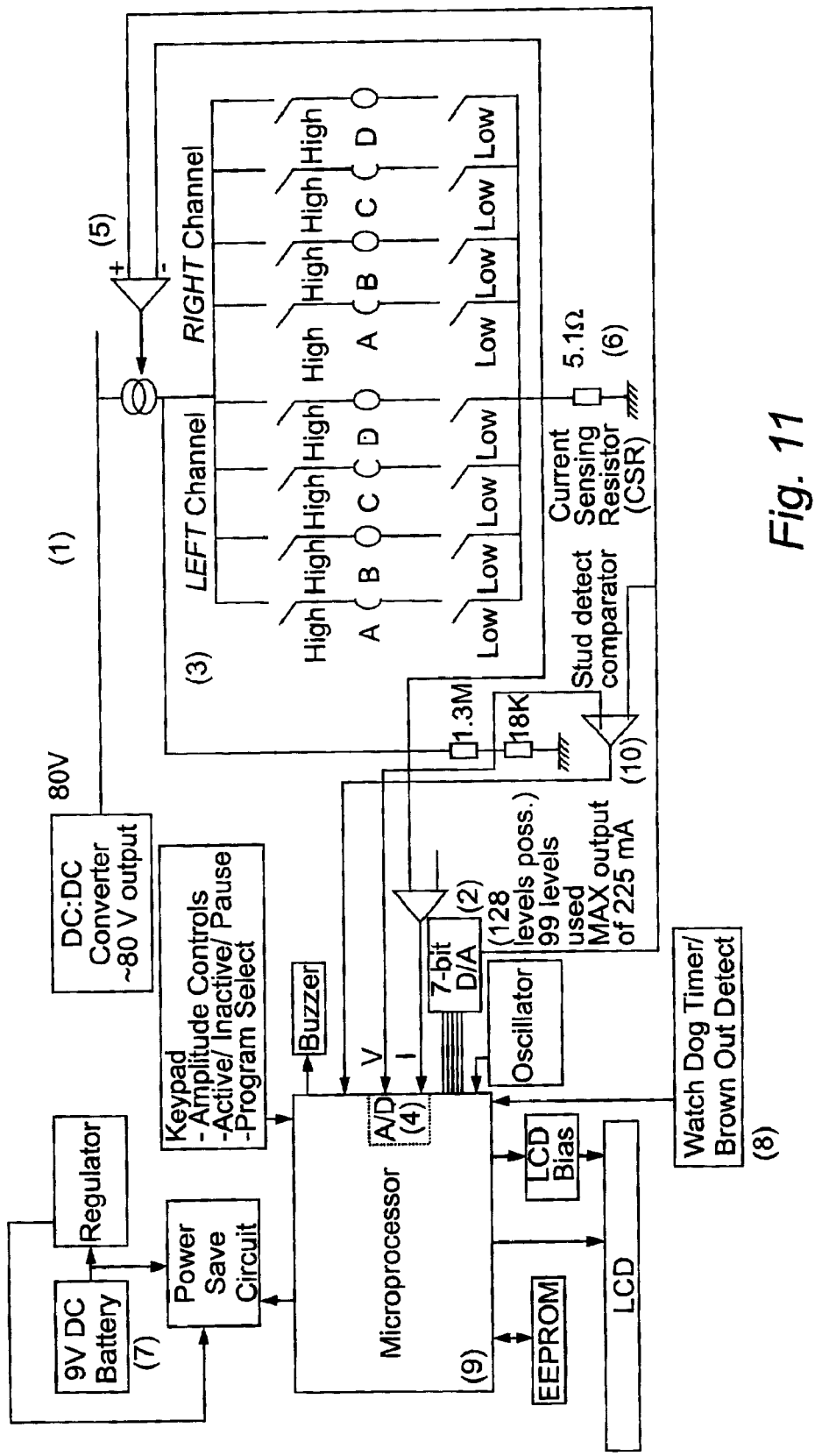
FIG. 11 shows a more detailed implementation of the apparatus of FIG. 10.

FIGS. 9 to 11 illustrate the apparatus aspect of the present invention in more detail.

As seen in FIG. 9, the basic requirement is that the electrodes 100 are connected in use to respective outputs 102 of a switching circuit 104 which can be operated such that for any given time period a given electrode will operate as a cathode, an anode, or neither. It is convenient to have a programmable control circuit 106 to control the switching.

FIG. 10 shows an array of output terminals 108 connected to an array of high side switches 110 and an array of low side switches 112. the output terminals 108 ultimately connect to respective electrodes on and/or in the body such that a potential created between the outputs causes a current to flow between the corresponding electrodes.

The switches 110 and 112 are high speed semiconductor devices capable of switching the required load currents of up to 200 mA and capable of withstanding the supply voltage which may be up to 200V. The switches are operable independently of each other by dedicated control signals 114 from a central processor 116.

In order to cause a current to flow between outputs 108a and 108b with output 108a being an anode and output 108b a cathode, switches 110a and 112b are turned on while switches 110b and 112a are turned off. To reverse the current through the same output terminals, 110b and 112a are turned on while 110a and 112b are turned off. Clearly it is possible in this way to establish any of the outputs 108 as anodes by setting their corresponding switch 110 on, and to establish any of the outputs 108 as a cathode by turning the respective 112 on. An output terminal is off, or electrically inactive, if both its high side switch 110 and its low side switch 112 are turned off.

It is possible to rapidly change the designation of anode, cathode or inactive by controlling the corresponding signal lines 114. Each stimulation pulse can in this way be divided into time periods where a unique anode-cathode configuration can be set up for each time period.

A constant current controlled pulse is produced under the control of the CPU 116, which produces a signal voltage representing the required current through a digital to analogue converter 118. This voltage is applied to a constant current control circuit 120 which compares it with a voltage which is representative of the total current flowing through the load as developed across current sense resistor 122. The resultant current pulse is applied to the output switch array which acts as a current steering network.

A voltage pulse generator could alternatively be used as an input to the switching array.

Moreover, more than one D/A converter 118 and pulse generator 120 could be provided, which could have an additional switching array to connect selected ones of the set of pulse generators to selected elements of the output steering array.

In the invention, a current pulse is divided into a number of time periods. A unique configuration of anodes and cathodes can be selected for each time period, and the duration and number of time slots is controllable, in addition to the current magnitude for each item period.

The data representing the pattern of anode and cathode selection, the duration of each time period, the number of time periods in the pulse, and the current magnitude for each time period is stored in data memory 124. To create a pulse, the CPU 116 reads the data describing the pulse, and starts with the data representing the first time period of the pulse. The CPU 116 outputs the required current level to the D/A converter 118 and selects the required anode and cathode pattern on signal lines 114. The CPU 116 maintains these signals for the specified duration of the first time period of the pulse, whereupon it sets up the current level and switch pattern for the next time period of the pulse. It continues this process until the last specified time period of the stimulation pulse has been completed. The CPU 116 then turns all signal lines 114 off and sets the D/A converter 118 to zero, thereby terminating the pulse.

A user interface is provided through keypad 126 and display 128. Application software can be provided which allows the user to set up pulse definition data or to select between a set of predefined pulse definition tables. The information defining the time period electrode pattern sequence can also be entered through interface to other electronic information sources such as computers and remote control devices.

The CPU 118 may operate in a closed loop mode where it alters the time period electrode pattern sequence in response to signals derived from the effect generated by the stimulation. For example, a signal representative of the force generated in the stimulated muscle could be provided and the CPU programmed to automatically adjust and/or search for switching patterns which maximise the force signal or regulate it to a set level. More especially, two or more force sensors could be provided and the CPU programmed to produce force differential between the force sensors by discrimination of the region and/or nerve type stimulated.

FIG. 11 is included to show an 8-channel implementation of FIG. 10 in somewhat more detail.

The present invention thus provides a method and apparatus for the stimulation of nerve or other tissues which gives much greater control and specificity than the prior art, by controlling the time element and varying the polarity of the pulse during a pulse phase.

The invention is not limited to the embodiments described herein which may be modified or varied without departing from the scope of the invention as defined in the claims.

TABLE 1

|  | Time Slot 1 | Time Slot 2 | Time Slot 3 | Time Slot 4 |
|---|---|---|---|---|
| Example 102 | | | | |
| A | H | | | |
| B | H | | | |
| C | L | | | |
| D | X | | | |
| Example 103 | | | | |
| A | H | | | |
| B | H | | | |
| C | L | | | |
| D | H | | | |
| Example 104 | | | | |
| A | H | X | | |
| B | X | H | | |
| C | L | L | | |
| D | X | X | | |

TABLE 1-continued

|  | Time Slot 1 | Time Slot 2 | Time Slot 3 | Time Slot 4 |
|---|---|---|---|---|
| Example 106 | | | | |
| A | H | X | | |
| B | H | X | | |
| C | L | L | | |
| D | X | H | | |
| Example 107 | | | | |
| A | H | H | X | |
| B | H | X | X | |
| C | H | H | H | |
| D | L | L | L | |
| Example 108 | | | | |
| A | H | X | H | |
| B | X | X | X | |
| C | H | H | H | |
| D | L | L | L | |
| Example 110 | | | | |
| A | L | X | X | |
| B | X | X | L | |
| C | X | L | X | |
| D | X | X | X | |
| E | X | X | X | |
| F | X | X | X | |
| G | X | X | L | |
| H | X | X | X | |
| I | X | X | X | |
| J | H | X | X | |
| K | X | H | X | |
| L | X | X | H | |

TABLE 2

| Warm up: | | | | |
|---|---|---|---|---|
| Pad Time 4 | Time 1 | Time 2 | Time 3 | Time 4 |
| A | H | H | H | H |
| B | L | L | L | L |
| C | H | H | H | H |
| D | L | L | L | L |
| time | 50 | 50 | 50 | 50 |
| Pad | Time 1 | Time 2 | Time 3 | Time 4 |
| A | H | H | H | L |
| B | H | H | L | H |
| C | H | L | H | H |
| D | L | H | H | H |
| time | 50 | 50 | 50 | 50 |
| Treatment: | | | | |
| Pad Time 4 | Time 1 | Time 2 | Time 3 | Time 4 |
| 1 | | | | |
| A | H | H | H | H |
| B | L | L | L | X |
| C | X | X | H | X |
| D | H | X | X | L |
| time | 100 | 100 | 300 | 125 |
| Pad | Time 1 | Time 2 | Time 3 | Time 4 |
| 2 | | | | |
| A | H | H | H | H |
| B | X | L | L | X |
| C | X | X | H | X |

TABLE 2-continued

| Pad | | | | |
|---|---|---|---|---|
| D | L | X | X | L |
| time | 100 | 100 | 300 | 125 |

| Pad Time 4 | Time 1 | Time 2 | Time 3 | Time 4 |
|---|---|---|---|---|
| 3 | | | | |
| A | H | H | H | H |
| B | X | L | L | X |
| C | X | X | H | X |
| D | L | X | X | L |
| time | 50 | 100 | 350 | 125 |

| Pad Time 4 | Time 1 | Time 2 | Time 3 | Time 4 |
|---|---|---|---|---|
| 4 | | | | |
| A | X | H | H | H |
| B | H | L | L | X |
| C | L | X | H | X |
| D | X | X | X | L |
| time | 100 | 200 | 225 | 100 |

| Pad Time 4 | Time 1 | Time 2 | Time 3 | Time 4 |
|---|---|---|---|---|
| 5 | | | | |
| A | X | H | H | H |
| B | H | L | L | X |
| C | L | X | H | X |
| D | X | X | X | L |
| time | 75 | 200 | 275 | 75 |

| Pad Time 4 | Time 1 | Time 2 | Time 3 | Time 4 |
|---|---|---|---|---|
| 6 | | | | |
| A | L | X | H | H |
| B | H | H | L | X |
| C | X | L | H | X |
| D | H | X | X | L |
| time | 250 | 50 | 250 | 100 |

| Pad Time 4 | Time 1 | Time 2 | Time 3 | Time 4 |
|---|---|---|---|---|
| 7 | | | | |
| A | X | H | H | H |
| B | H | L | L | X |
| C | L | X | H | X |
| D | X | X | X | L |
| time | 75 | 200 | 275 | 150 |

| Pad Time 4 | Time 1 | Time 2 | Time 3 | Time 4 |
|---|---|---|---|---|
| 8 | | | | |
| A | H | H | H | H |
| B | X | L | L | X |
| C | X | X | H | X |
| D | L | X | X | L |
| time | 50 | 100 | 300 | 125 |

| Pad Time 4 | Time 1 | Time 2 | Time 3 | Time 4 |
|---|---|---|---|---|
| 9 | | | | |
| A | H | H | H | X |
| B | L | L | L | L |
| C | X | X | H | H |
| D | X | X | X | X |
| time | 150 | 150 | 150 | 100 |

TABLE 3

| | Time Slot 1 | Time Slot 2 | Time Slot 3 | Time Slot 4 | |
|---|---|---|---|---|---|
| Example #1 | | | | | |
| A | H | H | H | | Both legs contracting |
| B | L | L | L | | |
| C | X | X | X | | |
| D | X | X | X | | |
| Duration | 30 | 30 | 30 | | |
| Example #2 | | | | | |
| A | H | H | H | | Can get contraction in right |
| B | L | X | X | | leg (A pad) and no sensation |
| C | X | L | X | | (touch or muscle) in left leg |
| D | X | X | L | | |
| Duration | 30 | 30 | 30 | | |
| Example #3 | | | | | |
| A | L | L | L | | |
| B | H | X | X | | |
| C | X | H | X | | |
| D | X | X | H | | |
| Duration | 30 | 30 | 30 | | |
| Example #4 | | | | | |
| A | H | L | L | | Contraction in right leg versus |
| B | L | X | X | | previous |
| C | X | H | X | | (A H, H, H much stronger and |
| D | X | X | H | | L, L, L much stronger) |
| Duration | 30 | 30 | 30 | | |
| Example #5 | | | | | |
| A | H | L/H/X | L | H | A: H, L, L, H |
| B | L | H/L/X | L | L | B: L, H, L, L |
| C | X | X | H | X | C-, -, H, - |
| D | X | X | X | X | |
| Duration | 30 | 30 | 30 | 30 | |
| Example #6 | | | | | |
| A | H | H | H/L | H | When A is H, H, H, H there is |
| B | L | L | L/H | L | a much stronger contraction in |
| C | X | X | X | X | both legs than when A is H, |
| D | X | X | X | X | H, L, H and is also stronger |
| Duration | 30 | 30 | 30 | 30 | than Example #6b |
| Example #6b | | | | | |
| A | H | H | X | H | Can get contraction in right |
| B | L | L | L | L | leg (A pad) and no sensation |
| C | X | X | H | X | (touch or muscle) in left leg |
| D | X | X | X | X | |
| Duration | 30 | 30 | 30 | 30 | |

What is claimed is:

1. Apparatus for applying pulsed electrical stimulation to a human or animal subject, the apparatus comprising a control circuit having a number of output terminals each of which is connectable, in use, to at least one of an array (greater than two) of electrodes placed on and/or in the subject; the control circuit including means for providing stimulation pulses to two or more of the electrodes simultaneously whereby the pulses are subdivided into a plurality of contiguous time periods, and for each time period, each output terminal may be connected as either anode, cathode or neither to provide discrimination between stimulated and non-stimulated regions of tissue and/or nerve types of the subject by controlling the time-summated current flow applied via each electrode during each pulse.

2. Apparatus according to claim 1 wherein the control circuit is operable such that the current during a single time period is unlikely to stimulate any tissue and/or any nerve type of the subject.

3. Apparatus according to claim 1 wherein the control circuit is operable such that the current during a single time period is unlikely to stimulate tissue in a preselected region and/or nerve type, but the time-summated current over a number of time periods is likely to stimulate another preselected region and/or nerve type.

4. Apparatus according to claim 1 wherein the control circuit is operable such that the current during a single time period is unlikely to stimulate a selected region of tissue and/or a selected nerve type, but the time-summated current over a number of time periods is likely to stimulate said selected region of tissue and/or said selected nerve type.

5. Apparatus according to claim 1 wherein the control circuit is operable to generate a time period electrode pattern which favours the stimulation of a selected region of tissue and/or a selected nerve type.

6. Apparatus according to claim 1 wherein the control circuit is operable such that the user may select a sequence of time period electrode patterns which favours the stimulation of a preselected region and/or nerve type.

7. Apparatus according to claim 1 wherein a train of pulses is generated and the control circuit is operable such that some of the pulses within the train of pulses may have different time period electrode current patterns.

8. Apparatus according to claim 1 wherein the circuit is operable such that the individual time period durations and/or the number of time periods per pulse are variable.

9. Apparatus according to claim 1 wherein there is included means to set the same or different total current in each time period within a pulse.

10. Apparatus according to claim 1 wherein there is included means to set the current level at each output in each time period within a pulse.

11. Apparatus according to claim 1 wherein the control circuit is operable such that the current through each output is a biphasic waveform with net zero direct current component.

12. Apparatus according to claim 1 wherein the control circuit is operable such that the current through a selected output or outputs has a predetermined DC component.

13. Apparatus according to claim 1 wherein the control circuit is operable such that the time period electrode pattern sequence creates a current density waveform in selected tissue which preferentially stimulates selected nerve types with matching temporal stimulation characteristics.

14. Apparatus for applying electrical stimulation to a human or animal subject, the apparatus comprising a control circuit having a number of outputs each of which is connectable, in use, to a respective one of an array (greater than two) of electrodes placed on and/or in the subject; the control circuit being arranged to generate stimulation pulses for application via two or more of the electrodes to the subject simultaneously; the pulses being subdivided into a plurality of contiguous time periods, and the control circuit including means for selectively connecting the outputs for each time period such that each of the electrodes act as anode(s) or cathode(s) or neither to provide discrimination between stimulated and non-stimulated regions of tissue and/or nerve types of the subject by controlling the time-summated current flow applied via each electrode during each pulse.

15. Apparatus according to claim 14, wherein the control circuit is operable such that during at least one time period the pulse is applied simultaneously across a plurality of outputs at one polarity and one other output at the opposite polarity such that a number of electrodes act as anodes and one electrode as a common cathode, or vice versa, whereby the intensity of the current in the region of the electrodes connected to said plurality of outputs is insufficient to stimulate that region whereas the intensity of the current in the region of the electrode connected to said one output is sufficient to stimulate the latter region.

16. Apparatus according to claim 14, wherein the control circuit is operable such that during different time periods the pulse is applied across respective different outputs of one polarity and a single output of opposite polarity such that electrodes connected to said different outputs act as anodes and one electrode connected to said single output acts as a cathode, or vice versa, whereby the duration of the current in the region of the electrodes connected to said different outputs is insufficient to stimulate that region whereas the duration of the current in the region of the electrode connected to said single output is sufficient to stimulate the latter region.

17. Apparatus according to claim 14, in which the pulse is applied across different combinations of outputs in different time periods to preferentially stimulate at least two different regions of the subject in said different time periods.

18. Apparatus according to claim 14, in which the pulse is applied across different combinations of outputs in different time periods to preferentially stimulate at least one region of the subject with different levels of stimulation during said different time periods.

19. Apparatus according to claim 14, in which the control circuit operates such that the total current flowing, in use, across the electrodes is substantially constant over all time periods of a pulse.

20. Apparatus according to claim 14, in which the control circuit operates such that the total current flowing, in use, across the electrodes differs for at least one time period of a pulse.

21. Apparatus according to claim 14, in combination with an array of electrodes connected to said outputs.

22. Apparatus according to claim 21, in which at least one electrode has a different area to the others.

23. Apparatus according to claim 14, in which at least two of the electrodes are intertwined.

24. Apparatus according to claim 14, including memory means for storing timeslot pattern sequence data.

25. A method of applying electrical stimulation to a human or animal subject, comprising placing a plurality of spaced stimulation electrodes on and/or in the subject, each electrode being capable of selectively acting as an anode, a cathode or neither, and applying electrical stimulation pulses to the subject via a plurality of electrodes simultaneously; the duration of each pulse comprising a plurality of contiguous time periods during each of which none, some or all of the electrodes are selected to act as anode(s) or cathode(s) or neither to provide discrimination between stimulated and non-stimulated regions of tissue and/or nerve types of the subject by controlling the time-summated current flow applied via each electrode during each pulse.

26. A method according to claim 25, wherein during at least one time period the pulse is applied simultaneously across a plurality of electrodes at one polarity and at least one other common electrode of the opposite polarity whereby the intensity of the current in the region of said plurality of electrodes is insufficient or unlikely to stimulate that region whereas the intensity of the current in the region of the common electrode is sufficient to stimulate the latter region.

27. A method according to claim 25, wherein during different time periods the pulse is applied across respective different electrodes of one polarity and a common electrode of opposite polarity, whereby the duration of the current in the region of said different electrodes is insufficient or unlikely to stimulate that region whereas the duration of the current in the region of the common electrode is sufficient to stimulate the latter region.

28. A method according to claim 25, in which the pulse is applied across different combinations of electrodes in different time periods to preferentially stimulate at least two different regions and/or nerve types of the subject in said different time periods.

29. A method according to claim 25, in which the pulse is applied across different combinations of electrodes in different time periods to preferentially stimulate at least one region and/or nerve type of the subject with different levels of stimulation during said different time periods.

30. Apparatus according to claim 1, including memory means for storing timeslot pattern sequence data.

* * * * *